US008470574B2

(12) United States Patent
Toda et al.

(10) Patent No.: US 8,470,574 B2
(45) Date of Patent: Jun. 25, 2013

(54) L-SUCCINYLAMINOACYLASE AND PROCESS FOR PRODUCING L-AMINO ACID USING IT

(75) Inventors: Atsushi Toda, Tsuruga (JP); Sachio Iwai, Tsuruga (JP); Yoshiaki Nishiya, Tsuruga (JP); Takeshi Miyata, Hachimantai (JP); Aya Oosato, Hachimantai (JP); Shinya Kumagai, Hachimantai (JP); Toshihide Yamada, Hachimantai (JP)

(73) Assignees: Toyo Boseki Kabushiki Kaisha, Osaka-shi, Osaka (JP); Sekisui Medical Co., Ltd., Tokyo (JP)

( * ) Notice: Subject to any disclaimer, the term of this patent is extended or adjusted under 35 U.S.C. 154(b) by 296 days.

(21) Appl. No.: 12/989,728

(22) PCT Filed: May 7, 2009

(86) PCT No.: PCT/JP2009/002006
§ 371 (c)(1),
(2), (4) Date: Oct. 26, 2010

(87) PCT Pub. No.: WO2009/136500
PCT Pub. Date: Nov. 12, 2009

(65) Prior Publication Data
US 2011/0244530 A1 Oct. 6, 2011

(30) Foreign Application Priority Data
May 7, 2008 (JP) ................................. 2008-121244

(51) Int. Cl.
*C12N 9/14* (2006.01)
*C07K 1/00* (2006.01)
(52) U.S. Cl.
USPC ............ 435/195; 435/183; 435/106; 530/350
(58) Field of Classification Search
None
See application file for complete search history.

(56) References Cited

FOREIGN PATENT DOCUMENTS

| JP | 62-44181 A | 2/1987 |
|----|------------|--------|
| JP | 5-328972 A | 12/1993 |
| JP | 2006-055131 A | 3/2006 |
| JP | 2006-067870 A | 3/2006 |
| JP | 2008-061642 A | 3/2008 |
| JP | 2008-307006 A | 12/2008 |
| WO | 2009-136500 A1 | 11/2009 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Amersham Protein Purification Handbook, Oct. 2001, p. 59.
English-language translation of JP62-44181, Nov. 2011, 15 pages.
Notification of Transmittal of Translation of the International Preliminary Report on Patentability (Form PCT/IB/338) of International Application No. PCT/JP2009/002006 mailed Dec. 23, 2010 with Forms PCT/IB/373 and PCT/ISA/237.
Takami, H. et al "Accession: Q5L1H1, Definition: Amidohyrolase," NCBI sequence Revision History, Oct. 31, 2006.
Feng, L. et al "Accession: YP_001124936, Definition: Amidohydrolase [*Geobacillus thermodenitrificans* NG80-2]," NCBI sequence Revision History, Dec. 12, 2007.
Batisse, N. et al "Two Amino Acid Amidohydrolase Genes Encoding L-Stereospecific Cabamoylase and Aminoacylase Are Organized in a Common Operon in *Bacillus stearothermophilus*," Applied and Environmental Microbiology, Feb. 1997, vol. 63 No. 2, pp. 763-766.
Cho, Hong-Yon et al "Thermostable Dipeptidase from *Bacillus stearothermophilus*: Its Purification, Characterization, and Comparison with Aminoacylase," J. Biochem, Received for publication Sep. 1, 1987, vol. 103 No. 4, pp. 622-628.
Feng, Lu et al "Genome and proteome of long-chain alkane degrading *Geobacillus thermodentrificans* NG80-2 isolated from a deep-subsurface oil reservoir," Proceedings of the National Academy of Sciences USA, Mar. 27, 2007, pp. 5602-5607.
International Search Report of PCT/JP2009/002006, mailing date Aug. 18, 2009.
Kumagai, Shinya et al "Defluvibacter sp. A131-3-kabu ga Sansei suru Shinki D-aminoacylase no Seisei to Shoseishitsu," Japan Society for Bioscience, Biotechnology, and Agrochemistry 2004 Nendo Taikai Koen Yoshishu, Mar. 5, 2004, p. 119 2B04p19.
Feng , L., et al. "Amidohydrolase [*Geobacillus thermodenitrificans* NG80-2].", NCBI Sequence Revision History [online]; Accession: 001124936, <http://www.nchi.nlm.nih.gov/sviewer/viewer.fcgi?138894483:NCBI:23439857> Jul. 29, 2008 uploaded, [retrieved on Feb. 23, 2010].
Lucas S., et al., "*Geobacillus* sp. G11MC16 ctg12, whole genome shotgun sequence.", NCBI Sequence Revision History [online]; Accession : NZ_ABVH 0100001, <http://www.ncbi.nlm.nih.gov/sviewer/viewer.fcgi?196247544: WGS:28954631>,Aug. 15, 2008 uploaded, [retrieved on Feb. 23, 2010].
Sakai A. et al., "Evolution of enzymatic activities in the enolase superfamily: N-succinylamino acid racemase and a new pathway for the irreversible conversion of D- to L-amino acids.", Biochemistry, 2006, 45(14), 4455-62.

(Continued)

*Primary Examiner* — Richard Hutson
(74) *Attorney, Agent, or Firm* — Westerman, Hattori, Daniels & Adrian, LLP

(57) ABSTRACT

The present invention provides an L-aminoacylase which is able to produce L-tert-leucine being useful as an intermediate for pharmaceuticals.
A protein which is characterized in being represented by any of the following (a) to (d): (a) a protein coded by a gene consisting of a nucleic acid sequence shown in SEQ ID No: 1; (b) a protein consisting of an amino acid sequence shown in SEQ ID No: 2; (c) a protein coded by a polynucleotide which hybridizes under a stringent condition with a nucleic acid sequence which is complementary to the nucleic acid sequence shown in SEQ ID No: 1 and having an L-succinylaminoacylase activity; and (d) a protein which consists of an amino acid sequence where one or several amino acid (s) is/are substituted, deleted, inserted and/or added in the protein consisting of the amino acid sequence shown in SEQ ID No: 2 and has an L-succinylaminoacylase activity.

8 Claims, 3 Drawing Sheets

OTHER PUBLICATIONS

"Amidohydrolase [*Geobacillus* sp. G11MC16].", NCBI Sequence Revision History[online]; Accession:ZP_03146617, <http://www.ncbi.nlm.nih.gov/sviewer/viewerfcgi?196247915:WGS:28954631>, Aug. 15, 2008 uploaded, [retrieved on Feb. 19, 2010].

Nazina TN., et al., "Taxonomic study of aerobic thermophilic bacilli: descriptions of *Geobacillus subterraneus* gen. nov., sp. nov. and *Geobacillus uzenensis* sp. nov. from petroleum reservoirs and transfer of *Bacillus stearothermophilus, Bacillus thermocatenulatus, Bacillus thermoleovorans, Bacillus Kaustophilus, Bacillus thermoglucosidasius* and *Bacillus thermodenitrificans* to *Geobacillus* as the new combinations *G. stearothermophilus, G. thermocatenulatus, G. thermoleovorans, G. kaustophilus, G. thermoglucosidasius* and *G. thermodenitrificans*." Int., Int. J. of System. Evol. Microbiology, 51, pp. 433-446, 2001.

Inernational Search Report of PCT/JP2009/006770, dated of mailing Mar. 9, 2010.

UniProt Accession No. B4B154, Sep. 2008, 1 page.

Definition of "represent", obtained from Merriam-Webster online dictionary at www.merriam-webster.com, last viewed on Nov. 14, 2011.

* cited by examiner

[Fig. 1]
[Fig. 2]
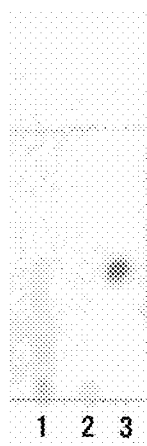

[Fig. 3]
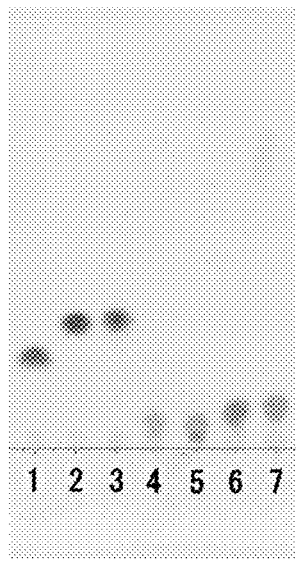
1 2 3 4 5 6 7
[Fig. 4]
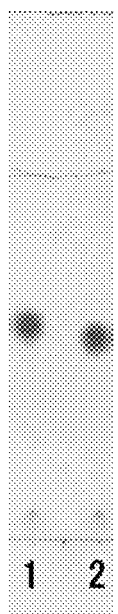
1 2

[Fig. 5]
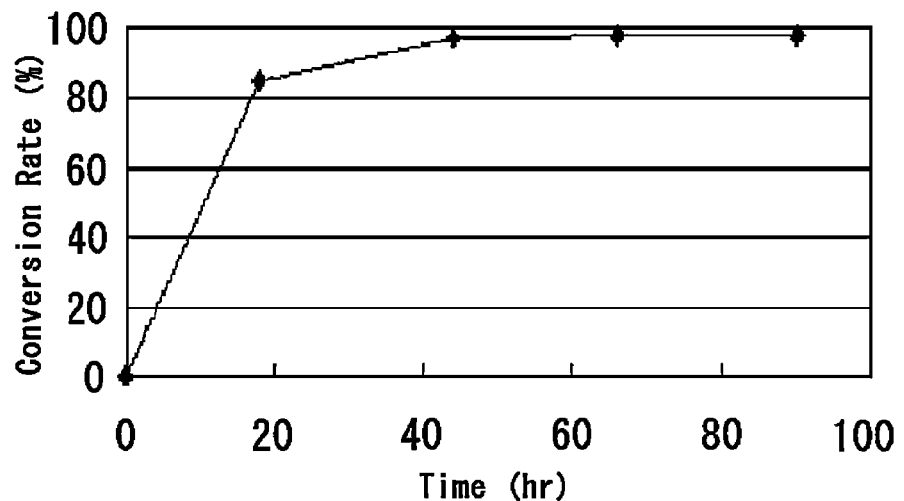
[Fig. 6]
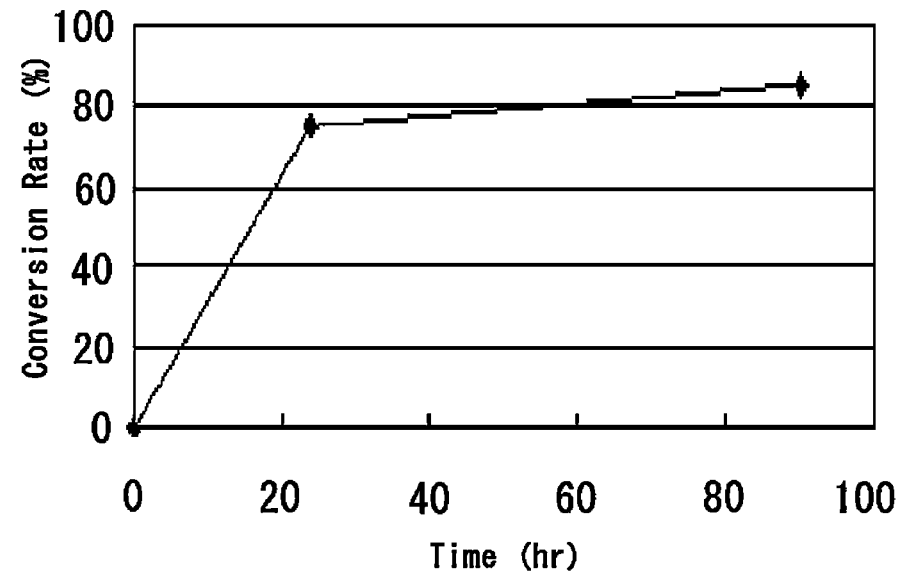

```
                        SEQUENCE LISTING

<160> NUMBER OF SEQ ID NOS: 7

<210> SEQ ID NO 1
<211> LENGTH: 1161
<212> TYPE: DNA
<213> ORGANISM: Geobacillus stearothermophilus
<220> FEATURE:
<221> NAME/KEY: CDS
<222> LOCATION: (1)..(1161)

<400> SEQUENCE: 1 atg aaa gaa atc gtt gag cag atg aaa gcg gag cta tgg gag gtt ttc      48
Met Lys Glu Ile Val Glu Gln Met Lys Ala Glu Leu Trp Glu Val Phe
  1               5                  10                  15 gat cac ctt cac cgc cat cca gaa atc agc tgg gaa gag tgg caa acg      96
Asp His Leu His Arg His Pro Glu Ile Ser Trp Glu Glu Trp Gln Thr
             20                  25                  30 act gaa ttt ctc cgc cga gag ttg gag cgc gaa gga tat cgg gtg cgg     144
Thr Glu Phe Leu Arg Arg Glu Leu Glu Arg Glu Gly Tyr Arg Val Arg
         35                  40                  45 acg ttt gcc gat tgc ccg ggt gtg gtg gcg gaa atc ggc gcc ggg ccg     192
Thr Phe Ala Asp Cys Pro Gly Val Val Ala Glu Ile Gly Ala Gly Pro
     50                  55                  60 ttt acg gtt ggg gtg cgc agc gat atg gat gcg ctt tgg caa gaa gtg     240
Phe Thr Val Gly Val Arg Ser Asp Met Asp Ala Leu Trp Gln Glu Val
 65                  70                  75                  80 aac ggc gtt tgg cag ccg aac cat gcg tgc ggg cat gat gcc cac atg     288
Asn Gly Val Trp Gln Pro Asn His Ala Cys Gly His Asp Ala His Met
                 85                  90                  95 acg atc gtg ctc ggg gtg gcg aag ctg ctt cgc cgc atc ggc tat gag     336
Thr Ile Val Leu Gly Val Ala Lys Leu Leu Arg Arg Ile Gly Tyr Glu
            100                 105                 110 ccg ccg ggg acg ctc cgg ttt ttg ttc cag ccg gcc gag gag aaa gga     384
Pro Pro Gly Thr Leu Arg Phe Leu Phe Gln Pro Ala Glu Glu Lys Gly
        115                 120                 125 aca ggg gcg tta aag ctg atc gaa aaa gga gcg gtc gac ggc gtg tcg     432
Thr Gly Ala Leu Lys Leu Ile Glu Lys Gly Ala Val Asp Gly Val Ser
    130                 135                 140 ttt tta tac ggc gtt cac ctg cgg ccg att caa gaa gtg aaa ggc gga     480
Phe Leu Tyr Gly Val His Leu Arg Pro Ile Gln Glu Val Lys Gly Gly
145                 150                 155                 160 tat gcg gcg ccg gcg atc atc cat ggg gcg gcg caa tgc atc gaa ggg     528
Tyr Ala Ala Pro Ala Ile Ile His Gly Ala Ala Gln Cys Ile Glu Gly
                165                 170                 175 cgg atc cgc ggt gtg gcg gcg cac gcg gcg cgg ccg cat tta ggc gtc     576
Arg Ile Arg Gly Val Ala Ala His Ala Ala Arg Pro His Leu Gly Val
            180                 185                 190 aat gtc att gaa gtc ggc agc gcc att gtg caa gag ctc ggc aaa att     624
Asn Val Ile Glu Val Gly Ser Ala Ile Val Gln Glu Leu Gly Lys Ile
        195                 200                 205 cat att gat ccg caa gtg ccg gcg tcg atc aaa atg acg aag ttt cac     672
His Ile Asp Pro Gln Val Pro Ala Ser Ile Lys Met Thr Lys Phe His
    210                 215                 220 gcc ggt gaa aaa gat gcg aac acg atc ccg ggc tac gcg gaa ttc gcc     720
Ala Gly Glu Lys Asp Ala Asn Thr Ile Pro Gly Tyr Ala Glu Phe Ala
225                 230                 235                 240
```

```
ctt gat ttg cgg gcg caa acg aac gag gcg atg gag cgg ctc gtt gaa      768
Leu Asp Leu Arg Ala Gln Thr Asn Glu Ala Met Glu Arg Leu Val Glu
            245                 250                 255 ggg cta cgt cat gtg atc aac ggg gtc gct gcc att tat ggg gcg gag      816
Gly Leu Arg His Val Ile Asn Gly Val Ala Ala Ile Tyr Gly Ala Glu
        260                 265                 270 att gaa cta gtg gaa cgg acg cgc atc gtc gcc gct cat cct gat cca      864
Ile Glu Leu Val Glu Arg Thr Arg Ile Val Ala Ala His Pro Asp Pro
        275                 280                 285 gat gcg gtg cgg ctg atg gag gag gcg att atc gcc gcc ttg ggg acg      912
Asp Ala Val Arg Leu Met Glu Glu Ala Ile Ile Ala Ala Leu Gly Thr
    290                 295                 300 gaa aaa tgc gtt ccg ccg gtt gtg aca tcg gga gga gag gat ttc cat      960
Glu Lys Cys Val Pro Pro Val Val Thr Ser Gly Gly Glu Asp Phe His
305                 310                 315                 320 ttt tat tcc ttt caa aaa ccg gag ctg aag aca acg atg ctc ggg tta     1008
Phe Tyr Ser Phe Gln Lys Pro Glu Leu Lys Thr Thr Met Leu Gly Leu
                325                 330                 335 ggc tgt gac ttg cgt ccg ggg ctc cat cac ccg aac atg acg ttc cgg     1056
Gly Cys Asp Leu Arg Pro Gly Leu His His Pro Asn Met Thr Phe Arg
            340                 345                 350 cgc gat gat ttg ctt tcc ggt gtg gaa att ttg gcg cga acg gtc atc     1104
Arg Asp Asp Leu Leu Ser Gly Val Glu Ile Leu Ala Arg Thr Val Ile
        355                 360                 365 aat acg ttt gcg ctg cag ggg gag aac gag cgt gtc tct gtc gct gca     1152
Asn Thr Phe Ala Leu Gln Gly Glu Asn Glu Arg Val Ser Val Ala Ala
        370                 375                 380 aat cat tga                                                         1161
Asn His
385

<210> SEQ ID NO 2
<211> LENGTH: 386
<212> TYPE: PRT
<213> ORGANISM: Geobacillus stearothermophilus

<400> SEQUENCE: 2

Met Lys Glu Ile Val Glu Gln Met Lys Ala Glu Leu Trp Glu Val Phe
 1               5                  10                  15

Asp His Leu His Arg His Pro Glu Ile Ser Trp Glu Glu Trp Gln Thr
            20                  25                  30

Thr Glu Phe Leu Arg Arg Glu Leu Glu Arg Glu Gly Tyr Arg Val Arg
        35                  40                  45

Thr Phe Ala Asp Cys Pro Gly Val Val Ala Glu Ile Gly Ala Gly Pro
    50                  55                  60

Phe Thr Val Gly Val Arg Ser Asp Met Asp Ala Leu Trp Gln Glu Val
65                  70                  75                  80

Asn Gly Val Trp Gln Pro Asn His Ala Cys Gly His Asp Ala His Met
                85                  90                  95

Thr Ile Val Leu Gly Val Ala Lys Leu Leu Arg Arg Ile Gly Tyr Glu
            100                 105                 110

Pro Pro Gly Thr Leu Arg Phe Leu Phe Gln Pro Ala Glu Glu Lys Gly
        115                 120                 125

Thr Gly Ala Leu Lys Leu Ile Glu Lys Gly Ala Val Asp Gly Val Ser
    130                 135                 140

Phe Leu Tyr Gly Val His Leu Arg Pro Ile Gln Glu Val Lys Gly Gly
145                 150                 155                 160

Tyr Ala Ala Pro Ala Ile Ile His Gly Ala Ala Gln Cys Ile Glu Gly
                165                 170                 175
```

-continued

```
Arg Ile Arg Gly Val Ala Ala His Ala Ala Arg Pro His Leu Gly Val
            180                 185                 190
Asn Val Ile Glu Val Gly Ser Ala Ile Val Gln Glu Leu Gly Lys Ile
        195                 200                 205
His Ile Asp Pro Gln Val Pro Ala Ser Ile Lys Met Thr Lys Phe His
    210                 215                 220
Ala Gly Glu Lys Asp Ala Asn Thr Ile Pro Gly Tyr Ala Glu Phe Ala
225                 230                 235                 240
Leu Asp Leu Arg Ala Gln Thr Asn Glu Ala Met Glu Arg Leu Val Glu
                245                 250                 255
Gly Leu Arg His Val Ile Asn Gly Val Ala Ala Ile Tyr Gly Ala Glu
            260                 265                 270
Ile Glu Leu Val Glu Arg Thr Arg Ile Val Ala Ala His Pro Asp Pro
        275                 280                 285
Asp Ala Val Arg Leu Met Glu Glu Ala Ile Ile Ala Ala Leu Gly Thr
    290                 295                 300
Glu Lys Cys Val Pro Pro Val Val Thr Ser Gly Gly Glu Asp Phe His
305                 310                 315                 320
Phe Tyr Ser Phe Gln Lys Pro Glu Leu Lys Thr Thr Met Leu Gly Leu
                325                 330                 335
Gly Cys Asp Leu Arg Pro Gly Leu His His Pro Asn Met Thr Phe Arg
            340                 345                 350
Arg Asp Asp Leu Leu Ser Gly Val Glu Ile Leu Ala Arg Thr Val Ile
        355                 360                 365
Asn Thr Phe Ala Leu Gln Gly Asn Glu Arg Val Ser Val Ala Ala
    370                 375                 380
Asn His
385

<210> SEQ ID NO 3
<211> LENGTH: 1128
<212> TYPE: DNA
<213> ORGANISM: Geobacillus stearothermophilus
<220> FEATURE:
<221> NAME/KEY: CDS
<222> LOCATION: (1)..(1128)

<400> SEQUENCE: 3 atg gcg atc aac atc gag tac gtc ata ttg cgc cat tta caa atg gag      48
Met Ala Ile Asn Ile Glu Tyr Val Ile Leu Arg His Leu Gln Met Glu
1               5                  10                  15 ttg aag gcg ccg ttt acg acg agc ttc ggc acg ttt caa agg aaa gag      96
Leu Lys Ala Pro Phe Thr Thr Ser Phe Gly Thr Phe Gln Arg Lys Glu
            20                  25                  30 ttg att tta gtg gaa gtt gtc gat cgc gac ggc gtt tcc ggc tgg ggc     144
Leu Ile Leu Val Glu Val Val Asp Arg Asp Gly Val Ser Gly Trp Gly
        35                  40                  45 gaa tcg gtc gca ttt tcc gcc ccg tgg tac agc gag gaa acg gtg aaa     192
Glu Ser Val Ala Phe Ser Ala Pro Trp Tyr Ser Glu Glu Thr Val Lys
    50                  55                  60 acg aac tgg cat atg ctc gaa gat ttc ctt gtg ccg ctt gcg ttg gct     240
Thr Asn Trp His Met Leu Glu Asp Phe Leu Val Pro Leu Ala Leu Ala
65                  70                  75                  80 gag ccg att cac cac ccg gag gag ctg tca aag cgc ttt tct gcc atc     288
Glu Pro Ile His His Pro Glu Glu Leu Ser Lys Arg Phe Ser Ala Ile
                85                  90                  95 cgc caa aac aac atg gcg aaa gcg gcg ctt gag ggg gcg gta tgg gat     336
Arg Gln Asn Asn Met Ala Lys Ala Ala Leu Glu Gly Ala Val Trp Asp
            100                 105                 110
```

| | | |
|---|---|---|
| ttg tac gcc aag cgg ctc ggc gtt ccg ctt tct caa gct ctc gga gga<br>Leu Tyr Ala Lys Arg Leu Gly Val Pro Leu Ser Gln Ala Leu Gly Gly<br>115                              120                            125 | | 384 |
| gcg aaa aag gac att gaa gtc ggc gtc agc atc ggc atc cag ccg acg<br>Ala Lys Lys Asp Ile Glu Val Gly Val Ser Ile Gly Ile Gln Pro Thr<br>130                              135                            140 | | 432 |
| gtt gcc gat ctg ctt cag gtg att gag cgg tat gtg gcg caa ggg tac<br>Val Ala Asp Leu Leu Gln Val Ile Glu Arg Tyr Val Ala Gln Gly Tyr<br>145                              150                            155                            160 | | 480 |
| cgg cgg atc aag gtg aaa atc aag cca agc tgg gat gtg gac gtc att<br>Arg Arg Ile Lys Val Lys Ile Lys Pro Ser Trp Asp Val Asp Val Ile<br>                          165                            170                            175 | | 528 |
| cgt gag gtg cgg cgc gtg ttt cct gac gtg ccg ctt atg gcc gat gcc<br>Arg Glu Val Arg Arg Val Phe Pro Asp Val Pro Leu Met Ala Asp Ala<br>                          180                            185                            190 | | 576 |
| aat tcg gcg tat acg ctt gtc gat gcg gat cgg ctg aaa gcg ctc gat<br>Asn Ser Ala Tyr Thr Leu Val Asp Ala Asp Arg Leu Lys Ala Leu Asp<br>                  195                            200                            205 | | 624 |
| gaa ttc ggg ttg ctg atg atc gag cag ccg ctc gcc gct gac gat ctt<br>Glu Phe Gly Leu Leu Met Ile Glu Gln Pro Leu Ala Ala Asp Asp Leu<br>210                              215                            220 | | 672 |
| gtc gat cac gct cgg ctg cag ccg ctt ctt cag acg ccg att tgc ctt<br>Val Asp His Ala Arg Leu Gln Pro Leu Leu Gln Thr Pro Ile Cys Leu<br>225                              230                            235                            240 | | 720 |
| gat gaa agc att cgt tcc tat gac gat gcg cgc aag gcg ctt gac ctt<br>Asp Glu Ser Ile Arg Ser Tyr Asp Asp Ala Arg Lys Ala Leu Asp Leu<br>                          245                            250                            255 | | 768 |
| ggc agc tgt cgc atc atc aac atc aaa atc ggg cgc gtt ggc ggg ctt<br>Gly Ser Cys Arg Ile Ile Asn Ile Lys Ile Gly Arg Val Gly Gly Leu<br>                  260                            265                            270 | | 816 |
| ggc gag gcg aag cgc atc cac gat ctt tgc gct gag cgc ggt gcg ccg<br>Gly Glu Ala Lys Arg Ile His Asp Leu Cys Ala Glu Arg Gly Ala Pro<br>275                              280                            285 | | 864 |
| gtc tgg tgc ggg ggg atg ctg gaa gca ggc gtc ggg cgc gcc cac aac<br>Val Trp Cys Gly Gly Met Leu Glu Ala Gly Val Gly Arg Ala His Asn<br>290                              295                            300 | | 912 |
| atc gcg atc acg acg ttg gaa aac ttc acc ctt ccc ggc gac acc gcc<br>Ile Ala Ile Thr Thr Leu Glu Asn Phe Thr Leu Pro Gly Asp Thr Ala<br>305                              310                            315                            320 | | 960 |
| gcg tcg tcg cat tat tgg gag cgg gat atc atc acg ccg gaa gtt gag<br>Ala Ser Ser His Tyr Trp Glu Arg Asp Ile Ile Thr Pro Glu Val Glu<br>                          325                            330                            335 | | 1008 |
| gtg cac ggc ggc ttg atc cgc gtg ccg gac gct ccc ggc atc ggc tat<br>Val His Gly Gly Leu Ile Arg Val Pro Asp Ala Pro Gly Ile Gly Tyr<br>                  340                            345                            350 | | 1056 |
| gac gtc gac cgc cgc caa gtg gag cgg tat acg cag ttt gcg aag gtg<br>Asp Val Asp Arg Arg Gln Val Glu Arg Tyr Thr Gln Phe Ala Lys Val<br>355                              360                            365 | | 1104 |
| ttt cat cgt acg gcg acg gca taa<br>Phe His Arg Thr Ala Thr Ala<br>          370                        375 | | 1128 |

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
aaggaggtaa aatggcgatc aacatcgagt ac                                        32

```
<210> SEQ ID NO 5
<211> LENGTH: 30
<212> TYPE: DNA
<213> ORGANISM: Artificial
<220> FEATURE:
<223> OTHER INFORMATION: Primer

<400> SEQUENCE: 5
tctagattat gccgtcgccg tacgatgaaa                                        30

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
aaacatatga agaaatcgt tgagcagatg                                         30

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
tctagatcaa tgatttgcag cgacag                                            26
```

L-SUCCINYLAMINOACYLASE AND PROCESS FOR PRODUCING L-AMINO ACID USING IT

TECHNICAL FIELD OF THE INVENTION

The present invention relates to a novel L-succinylaminoacylase derived from thermophilic bacteria and, more particularly, it relates to a novel L-succinylaminoacylase which is able to utilize N-succinyl-L-tert-leucine as a substrate and also to a process for producing an L-amino acid using this enzyme.

BACKGROUND ART

L-amino acids are useful in many industrial fields such as pharmaceuticals, agricultural chemicals and foods. With regard to the industrially useful L-amino acid for example, there have been known L-lysine, L-threonine, L-isoleucine and L-proline used as additives for animal feeds, ingredients for health foods, amino acid transfusion, etc.; L-arginine and L-ornithine used as ingredients for hepatic function promoters, amino acid transfusion and multi-amino acid preparations; L-histidine used as hepatic function promoters and precursor for histamine; L-phenylalanine used as a precursor for sweeteners; and L-tert-leucine used as an intermediate for various pharmaceuticals. Accordingly, there has been a demand for an efficient production of those useful L-amino acids in a state of being separated from D-amino acids.

As to a process for producing the L-amino acid, there has been a conventional method where a racemic N-acylamino acid is synthesized and then only an L-form compound in the racemic modification is hydrolyzed using an enzyme called an L-aminoacylase. In result, only L-amino acid is specifically produced. As to the L-aminoacylase used for that method, there have been known, for example, an L-aminoacylase derived from *Penicillium funiculosum* (Patent Document 1) and an L-aminoacylase derived from *Streptomyces mobaraensis* (Patent Document 2).

However, those L-aminoacylases are excellent in a hydrolyzing ability, their substrate specificity is still unsatisfactory whereby they are unable to recognize an N-acyl-L-tert-leucine as a substrate. Therefore, according to the method using conventional L-aminoacylase, an N-acyl-DL-tert-leucine is unable to be optically resolved and it has been impossible to produce L-tert-leucine which is a useful intermediate for pharmaceuticals.

PRIOR ART DOCUMENTS

Patent Documents

Patent Document 1: Japanese Patent Application Laid-Open (JP-A) No. 328972/93
Patent Document 2: Japanese Patent Application Laid-Open (JP-A) No. 2006-67870

DISCLOSURE OF THE INVENTION

Problem that the Invention is to Solve

The present invention has been created in a point of view of the current status of the prior art as such and an object thereof is to provide a novel L-aminoacylase which is able to produce L-tert-leucine being useful as an intermediate for pharmaceuticals.

Means for Solving the Problem

In order to achieve the above object, the present inventors have conducted extensive investigations for the substrate specificity of L-aminoacylases derived from various organisms and, as a result, the inventors have found that an L-succinylaminoacylase obtained from NCA 1503 strain of *Geobacillus stearothermophilus* which is a kind of thermophilic bacteria is able to utilize N-succinyl-L-tert-leucine as a substrate, determined its nucleic acid sequence and accomplished the present invention.

Thus, in accordance with the present invention, there is provided a protein which is characterized in being represented by any of the following (a) to (d).

(a) a protein coded by a gene consisting of a nucleic acid sequence shown in SEQ ID No: 1;
(b) a protein consisting of an amino acid sequence shown in SEQ ID No: 2;
(c) a protein coded by a polynucleotide which hybridizes under a stringent condition with a nucleic acid sequence which is complementary to the nucleic acid sequence shown in SEQ ID No: 1 and having an L-succinylaminoacylase activity; and
(d) a protein which consists of an amino acid sequence where one or several amino acid(s) is/are substituted, deleted, inserted and/or added in the protein consisting of the amino acid sequence shown in SEQ ID No: 2 and has an L-succinylaminoacylase activity.

In accordance with the present invention, there is further provided a gene which is characterized in being represented by any of the following (a) to (d).

(a) a gene which consists of the nucleic acid sequence shown in SEQ ID No: 1;
(b) a gene which codes for the protein consisting of the amino acid sequence shown in SEQ ID No: 2;
(c) a gene which hybridizes under a stringent condition with the nucleic acid sequence which is complementary to the nucleic acid sequence shown in SEQ ID No: 1 and codes for a protein having an L-succinylaminoacylase activity; and
(d) a gene which consists of a nucleic acid sequence corresponding to an amino acid sequence where one or several amino acid(s) is/are substituted, deleted, inserted and/or added in the protein consisting of the amino acid sequence shown in SEQ ID No: 2 and codes for a protein having an L-succinylaminoacylase activity.

In accordance with the present invention, there is furthermore provided a process for producing the above protein which is characterized in comprising steps of: inserting the above gene into a vector to prepare a recombinant vector; transforming a host cell using said recombinant vector to prepare a transformant; and culturing this transformant.

In accordance with the present invention, there is still further provided a process for producing an L-amino acid which is characterized in comprising a step of specifically hydrolyzing N-succinyl-L-amino acid in N-succinyl-DL-amino acid using the above-mentioned protein.

Advantages of the Invention

Unlike the L-aminoacylase which has been known conventionally, the L-succinylaminoacylase of the present invention is able to utilize N-succinyl-L-tert-leucine as a substrate whereby it is able to efficiently produce L-tert-leucine which is a useful intermediate for pharmaceuticals.

BRIEF DESCRIPTIONS OF DRAWINGS

FIG. 1 shows the result where production of L-tert-leucine by the L-succinylaminoacylase of the present invention is confirmed by means of TLC in Example 2.

FIG. 2 shows the result where production of L-tert-leucine by the commercially available L-aminoacylase is confirmed by means of TLC in Comparative Example.

FIG. 3 shows the result of detection of L-amino acid produced by the L-succinylaminoacylase of the present invention by means of TLC in Example 3.

FIG. 4 shows the result of detection of L-amino acid produced by the L-succinylaminoacylase of the present invention by means of TLC in Example 3.

FIG. 5 shows the result of measurement of the yield of L-tert-leucine produced by the L-succinylaminoacylase of the present invention by means of HPLC in Example 4. Time elapsed from the initiation of the reaction (hr) is shown in the abscissa while a conversion rate into L-tert-leucine (%) is shown in the ordinate.

FIG. 6 shows the result of measurement of the yield of L-tert-leucine produced by the L-succinylaminoacylase of the present invention by means of HPLC in Example 6. Time elapsed from the initiation of the reaction (hr) is shown in the abscissa while a conversion rate into L-tert-leucine (%) is shown in the ordinate.

BEST MODE FOR CARRYING OUT THE INVENTION

The L-succinylaminoacylase of the present invention is either (a) a protein coded by a gene consisting of a nucleic acid sequence shown in SEQ ID No: 1 or (b) a protein consisting of an amino acid sequence shown in SEQ ID No: 2. SEQ ID No: 1 is a nucleic acid sequence of L-succinylaminoacylase of NCA 1503 strain of *Geobacillus stearothermophilus* which is a kind of thermophilic bacteria while SEQ ID No: 2 is an amino acid sequence thereof.

The proteins of the above (a) and (b) have a characteristic that they are able to specifically hydrolyze only L-form compound of N-succinyl-L-amino acid among racemic N-succinylamino acid whereby L-amino acid is specifically produced. N-acetylamino acid and N-succinylamino acid are present in organisms. The above proteins (a) and (b) have at least 100-fold higher activity to N-succinylamino acid than to N-acetylamino acid. From the above, it can be said that the above proteins (a) and (b) are the enzymes which catalyze the reaction of producing L-amino acid and succinic acid by a specific hydrolysis of N-succinyl-L-amino acid or, in other words, they are L-succinylaminoacylases.

The biggest characteristic of the L-succinylaminoacylase of the present invention is that it is able to utilize N-succinyl-L-tert-leucine which is a kind of N-succinyl-L-non-natural amino acids. Since the L-aminoacylase which has been known conventionally is unable to utilize N-acyl-L-tert-leucine as a substrate, it is unable to produce L-tert-leucine. In contrast to the L-aminoacylase, L-succinylaminoacylase of the present invention is able to produce L-tert-leucine which is highly demanded as an intermediate for pharmaceuticals in a high yield. In the present specification, the term "yield" may be sometimes used in the same sense as the term "conversion rate".

Physical and chemical properties of the L-succinylaminoacylase of the present invention are as shown in the following (i) to (v).

(i) Molecular weight: 43 kDa (SDS-PAGE);

(ii) Substrate specificity: It reacts to N-succinyl-tert-leucine, N-succinylcyclohexylglycine and N-succinyl-4-bromophenylalanine;

(iii) Temperature stability: When it is subjected to a heating treatment for 30 minutes, it is stable at 70° C. and is inactivated at 75° C. or higher;

(iv) Optimum temperature: When it is made to react at pH 7 to 8, its action is optimum at the temperature of 55 to 60° C.; and (v) Optimum pH: When it is made to react at 60° C. for 30 minutes, its action is optimum at pH 7.

The L-succinylaminoacylase of the present invention exhibits its activity when divalent or univalent metal ion is made to react at the final concentration of 0.1 mM to 1 M therewith. Examples of the divalent or univalent metal ion include $Mn^{2+}$, $Co^{2+}$, $Mg^{2+}$, $Ca^{2+}$, $Ni^{2+}$ and $K^+$ and, among them, $Co^{2+}$ is particularly preferred. It has been known that, when $Co^{2+}$ is used, the activity increased to an extent of twice or more as compared with the case where $Zn^{2+}$ is used.

The present invention also covers (a) a gene consisting of the nucleic acid sequence shown in SEQ ID No: 1 and (b) a gene coding for the protein consisting of the amino acid sequence shown in SEQ ID No: 2. They are the genes corresponding to the proteins of the above (a) and (b).

The L-succinylaminoacylase of the present invention is not limited to the above (a) and (b), and covers (c) a protein coded by a polynucleotide which hybridizes under a stringent condition with a nucleic acid sequence which is complementary to the nucleic acid sequence shown in SEQ ID No: 1 and having an L-succinylaminoacylase activity or (d) a protein which consists of an amino acid sequence where one or several amino acid (s) is/are substituted, deleted, inserted and/or added in the protein consisting of the amino acid sequence shown in SEQ ID No: 2 and has an L-succinylaminoacylase activity. Also, the genes of the present invention covers (c) a gene which hybridizes under a stringent condition with the nucleic acid sequence which is complementary to the nucleic acid sequence shown in SEQ ID No: 1 and codes for a protein having an L-succinylaminoacylase activity or (d) a gene which consists of a nucleic acid sequence corresponding to an amino acid sequence where one or several amino acid (s) is/are substituted, deleted, inserted and/or added in the protein consisting of the amino acid sequence shown in SEQ ID No: 2 and codes for a protein having an L-succinylaminoacylase activity. That is because, even if the nucleic acid sequence of the gene coding for the protein is partially modified or even if the amino acid sequence of the protein is partially modified as a result thereof, it is often the case that they are functionally identical proteins. That is also because, when the gene of the L-succinylaminoacylase of the present invention is integrated into a host organism (such as *Escherichia coli*) other than the organism wherefrom the gene is derived to express the L-succinylaminoacylase of the present invention, it is often the case that the nucleic acid sequence of the L-succinylaminoacylase is modified in accordance with the codon usage of the above host organisms so that the expression efficiency of the L-succinylaminoacylase is enhanced.

The gene coding for the protein of the above (c) is able to be prepared by means of colony or plaque hybridization using a nucleic acid sequence being complementary to the nucleic acid sequence shown in SEQ ID No: 1 or a part thereof as a probe. The term "stringent condition" used in this description stands for the condition where the so-called specific hybridization occurs and non-specific hybridization does not occur. For example, it may be such a condition where only such a DNA having a homology of 60% or more, preferably 80% or more, more preferably 90% or more, more preferably 95% or more, more preferably 97% or more, more preferably 98% or more, and more preferably 99% or more to a nucleic acid sequence is specifically hybridized.

A stringent condition can be created by adjusting the salt concentration, temperature, etc. of a hybridization solution.

An example is that a pre-hybridization is carried at 42° C. for one night in a hybridization solution containing 25% of formamide (50% of formamide in the case of severer condition), 4×SSC, 50 mM of Hepes (pH 7), 10×Denhardt's solution and 20 μg/mL of modified salmon sperm DNA and, after that, a labeled probe is added thereto followed by keeping at 42° C. for one night to conduct the hybridization. The washing solution and the temperature condition during the washing conducted thereafter are at about "1×SSC, 0.1% SDS and 37° C.", and the severer condition is at about "0.5×SSC, 0.1% SDS and 42° C.", and the more severer condition is at about "0.2× SSC, 0.1% SDS and 65° C.". The above combinations of SSC and SDS with temperature condition are mere examples and persons skilled in the art are able to achieve the same stringency as above by appropriately combining the above or other factors (such as probe concentration, probe length or hybridization reaction time) determining the stringency of the hybridization. The fact whether the gene obtained by the hybridization is a gene which codes for the protein having an L-succinylaminoacylase activity is able to be confirmed, for example, by such a means that the resulting gene is introduced into Escherichia coli to prepare a transformant, the transformant is cultured to produce an enzyme protein, the enzyme protein is purified and added to N-succinyl-DL-amino acid and production of an L-amino acid is measured by chromatography or the like.

Further, the gene of the protein of the above (d) (i.e. the gene which consists of a nucleic acid sequence corresponding to an amino acid sequence where one or several amino acid(s) is/are substituted, deleted, inserted and/or added in the protein consisting of the amino acid sequence shown in SEQ ID No: 2 and codes for a protein having an L-succinylaminoacylase activity) is able to be obtained, for example, by modifying the nucleic acid sequence shown in SEQ ID No: 1 utilizing a commercially available kit such as KOD-Plus-Mutagenesis Kit (manufactured by Toyobo) or a PCR method. The enzyme reactivity of the manipulated gene coding L-succinylaminoacylase is able to be confirmed by the same method described above.

Production of the L-succinylaminoacylase of the present invention is able to be easily carried out by such a manner that the gene thereof is inserted into an appropriate vector to prepare a recombinant vector, an appropriate host cell is transformed using said recombinant vector to prepare a transformant and the resulting transformant is cultured.

There is no particular limitation for the vector so far as it is capable of retaining replication ability or of autonomous replication in various host cells which are prokaryotic and/or eukaryotic cells and examples thereof include plasmid vector, phage vector and virus vector. Preparation of the recombinant vector may be carried out by a conventional method and it is able to be easily conducted, for example, in such a manner that the vector as such is ligated to the gene of L-succinylaminoacylase of the present invention using an appropriate restriction enzyme and ligase, if necessary, together with linker or adaptor DNA. In the case of gene fragment which is prepared by amplification using a DNA polymerase which adds one base to the amplified terminal such as Taq polymerase, connection to the vector by means of TA cloning is also possible.

As to the host cells, those which have been known conventionally are able to be used and, although there is no particular limitation provided that a recombination expression system therefor has been established, preferred examples include microbes such as Escherichia coli, Bacillus subtilis, actinomycete, aspergillus or yeast as well as insect cells, animal cells and higher plants, more preferred examples are microbes and the particular preferred example is E. coli (such as K12 strain or B strain). Preparation of the transformant may be carried out according to the conventional method.

When the resulting transformant is cultured for a predetermined period under the appropriate culturing condition for the host cells, L-succinylaminoacylase of the present invention is expressed from the integrated gene and is accumulated in the transformant.

Although the L-succinylaminoacylase of the present invention accumulated in the transformant may be used without purification, a purified one may be used as well. As to a method for the purification, the conventionally known one may be used and, for example, it may be conducted by such a manner that the transformant after the culture or a cultured product thereof is homogenized in an appropriate buffer, a cell extract is prepared therefrom by treating with ultrasonic wave or surfactant and separating means usually utilized for separation and purification of protein are appropriately combined. Examples of the separating means as such include a method where the difference in solubility is utilized such as salting out or solvent precipitation method; a method where the difference in molecular weight is utilized such as dialysis, ultrafiltration, gel filtration, unmodified polyacrylamide gel electrophoresis (PAGE) or sodium dodecylsulfate-polyacrylamide gel electrophoresis (SDS-PAGE); a method where the charge is utilized such as ion-exchange chromatography or hydroxyapatite chromatography; a method where the specific affinity is utilized such as affinity chromatography; a method where the difference in hydrophobicity is utilized such as reverse phase high-performance liquid chromatography; and a method where the difference in isoelectric point is utilized such as isoelectric electrophoresis, although the present invention is not limited to the above-mentioned ones.

Now a method for producing the L-amino acid using the L-succinylaminoacylase of the present invention will be illustrated. The L-amino acid according to the present invention is produced by a step of specifically hydrolyzing N-succinyl-L-amino acid (L-form compound) in the N-succinyl-DL-amino acid (racemic modification) using the L-succinylaminoacylase of the present invention.

To be more specific, this step may be carried out by such a manner that the L-succinylaminoacylase of the present invention and N-succinyl-DL-amino acid which is the starting material are dissolved in an appropriate solution and the resulting reaction solution is made to react under an appropriate condition.

Distilled water may be enough for the solution to be used and, if necessary, a buffer such as phosphate or Tris may be used as well. When a buffer is used, its concentration is preferred to be 20 to 200 mM and the pH is preferred to be 6.5 to 8.

The L-succinylaminoacylase of the present invention is used preferably in a concentration of 5 to 500 mg/L (100 to 10000 U/L) in the reaction solution. Further, since the L-succinylaminoacylase of the present invention retains its activity by addition of divalent or univalent metal ion in the final concentration of 0.1 mM to 1 M (preferably 0.1 to 1 mM) as mentioned already, it is necessary to add divalent or univalent metal ion to the reaction solution. Examples of the divalent or univalent metal ion include $Mn^{2+}$, $Co^{2+}$, $Mg^{2+}$, $Ca^{2+}$, $Ni^{2+}$ and $K^+$ and, among them, $Co^{2+}$ is particularly preferred.

The N-succinyl-DL-amino acid which is to be made to react with the L-succinylaminoacylase of the present invention may be synthesized by various known methods such as a method mentioned in Sakai A., et al., *Biochemistry*, 2006, 45 (14), 4455 to 62. Type of the DL-amino acid used as a starting material may be appropriately selected depending upon the type of the L-amino acid to be produced and it may be the naturally existing 20 kinds of amino acids and derivatives thereof and the non-natural amino acid such as tert-leucine, cyclohexylglycine or 4-bromophenylalanine and derivatives thereof.

Although the concentration of the N-succinyl-DL-amino acid in the reaction solution is not particularly limited, it is usually 1% by weight to 30% by weight.

In the process for producing the L-amino acid of the present invention, although there is no particular limitation for the temperature at which the reaction solution is made to react so far as it is the temperature where the L-succinylaminoacylase of the present invention acts well, it is usually preferred to be 20 to 70° C., more preferred to be 30 to 60° C., and much more preferred to be 55 to 60° C. With regard to the pH upon the reaction, although there is no particular limitation so far as it is the pH where the L-succinylaminoacylase of the present invention acts well, it is usually preferred to be pH 4 to 10, and more preferred to be pH 6 to 9. Although the reaction time is not particularly limited, it is usually about from one to seven day(s). The reaction time may be appropriately selected experimentally by taking into consideration the type of the L-amino acid to be produced, the desired producing amount and yield, amounts of the enzyme and the substrate used and the ratio thereof, reaction temperature, reaction pH, etc.

It is preferred that the process for producing the L-amino acid of the present invention further includes a step of racemizing N-succinyl-D-amino acid using N-succinylaminoracemase to produce N-succinyl-L-amino acid. Since the L-succinylaminoacylase of the present invention specifically hydrolyzes only N-succinyl-L-amino acid in N-succinyl-DL-amino acid (racemic modification), another half of the racemic modification, which is N-succinyl-D-amino acid would be wasted. Accordingly, producing N-succinyl-L-amino acid by racemizing N-succinyl-D-amino acid with N-succinylaminoracemase enables all the remaining N-succinyl-D-amino acid to be converted into L-amino acid.

N-succinylamino acid racemase is an enzyme which catalyzes both of a reaction which converts an L-form compound of N-succinylamino acid to a D-form compound and a reaction which converts a D-form compound to an L-form compound and makes their ratio almost equal (racemization). There is no particular limitation for the N-succinylamino acid racemase used in the production process of the present invention so far as it is able to racemize the N-succinylamino acid and the conventionally known ones such as N-acylamino acid racemase mentioned in Japanese Patent Application Laid-Open (JP-A) No. 2007-82534 and N-acylamino acid racemase mentioned in Japanese Patent Application Laid-Open (JP-A) No. 2008-61642 may be used.

The racemization reaction of the N-succinyl-D-amino acid using the N-succinylamino acid racemase is carried out, for example, by mixing a reaction solution containing N-succinyl-D-amino acid, N-succinylamino acid racemase and buffer under the following condition. Although there is no particular limitation for the reaction temperature so far as it is the temperature where the used N-succinylamino acid racemase acts well, it is usually preferred to be 25 to 70° C., and more preferred to be 37 to 70° C. Although there is no particular limitation for the pH upon the reaction so far as it is the pH where the N-succinylamino acid racemase acts well, it is usually preferred to be pH 5 to 9, and more preferred to be pH 6.5 to 8. The N-succinylamino acid racemase is used preferably in a concentration of 5 to 500 mg/L (500 to 50000 U/L) in the reaction solution. The N-succinylamino acid racemase retains its activity by addition of divalent metal ion in the final concentration of 0.1 mM to 1 M (preferably 0.1 to 1 mM). Examples of the divalent metal ion include $Mn^{2+}$, $Co^{2+}$, $Mg^{2+}$, $Fe^{2+}$ and $Ni^{2+}$ and, among them, $Co^{2+}$ is particularly preferred. When $Co^{2+}$ is made to react at the final concentration of 0.1 mM to 1 M, it exhibits the activity of twice or more higher in terms of relative activity as compared with the case where $Mn^{2+}$ is made to react at the final concentration of 0.1 mM to 1 M. As to the buffer used for the reaction of the N-succinylamino acid racemase, the same buffers as those used for the reaction of the L-succinylaminoacylase may be used.

Although the above-mentioned racemization reaction by the N-succinylamino acid racemase and hydrolyzing reaction by the L-succinylaminoacylase may be carried out separately, they are preferred to be conducted simultaneously. When they are simultaneously conducted, the microscopic analysis thereof is that, firstly, an L-form compound in the N-succinyl-DL-amino acid is deacylated (hydrolyzed) by the L-succinylaminoacylase of the present invention to give the aimed L-amino acid. Since the racemic state no longer exists when the L-form compound of the substrate is consumed, the N-succinylamino acid racemase further promotes the converting reaction of the D-form compound to the L-form compound. The N-succinyl-L-amino acid produced by the N-succinylamino acid racemase is successively converted to the L-amino acid by the L-succinylaminoacylase of the present invention. As a result of the repetition thereof, nearly all of the N-succinyl-DL-amino acid is able to be converted to the L-amino acid theoretically. As to the reaction condition when racemization reaction and hydrolysis reaction are conducted simultaneously, although there is no particular limitation so far as it is within a range where the N-succinylamino acid racemase and the L-succinylaminoacylase of the present invention achieve the activity, it is preferred to conduct the reaction under the condition where the substrate concentration is 0.01 mM to 500 mM, the pH is 6 to 8 and the temperature is 30 to 60° C. As to the time needed for the racemization reaction and the hydrolyzing reaction, there is no particular limitation so far as it is such a time by which the N-succinyl-DL-amino acid used as the starting material is able to be converted to the L-amino acid in a desired amount and, although it varies depending upon the charged amount, it is usually about one to seven day(s).

EXAMPLES

The present invention will now be specifically illustrated by way of the following Examples although the present invention is not limited to the following Examples.

Synthesis of N-succinyl-L-amino acid (1) Synthesis of N-succinyl-L-tert-leucine

L-tert-Leucine (manufactured by Tokyo Kasei Kogyo) (10 g) was dissolved in 50 mL of water and 15 g of 20% sodium hydroxide solution (manufactured by Nakarai Tesk), then 8 g of succinic acid anhydride and 15 g of 20% sodium hydroxide solution (manufactured by Nakarai Tesk) were added thereto and the mixture was made to react at 20 to 40° C. with stirring. After the reaction solution was neutralized with hydrochloric acid, it was extracted with ethyl acetate and then concentrated. The concentrate was crystallized by addition of hexane thereto followed by drying to give 14 g of N-succinyl-L-tert-leucine as white powder.

(2) Synthesis of N-succinyl-L-valine

L-valine (manufactured by Nakarai Tesk) (10 g) was dissolved in 50 mL of water and 17 g of 20% sodium hydroxide solution (manufactured by Nakarai Tesk), then 8.8 g of succinic acid anhydride (manufactured by Nakarai Tesk) and 17 g of 20% sodium hydroxide solution (manufactured by Nakarai Tesk) were added thereto and the mixture was made to react at 20 to 40° C. with stirring. After the reaction solution was neutralized with hydrochloric acid (manufactured by Nakarai Tesk), it was extracted with ethyl acetate (manufactured by Nakarai Tesk) and then concentrated. The concentrate was crystallized by addition of hexane thereto followed by drying to give 15 g of N-succinyl-L-valine as white powder.

(3) Synthesis of N-succinyl-L-phenylalanine, N-succinyl-L-tryptophan, N-succinyl-L-asparagine, N-succinyl-L-aspartic acid, N-succinyl-L-serine, N-succinyl-L-glutamic acid, N-succinyl-L-cyclohexylglycine and N-succinyl-L-4-bromophenylalanine Those N-succinyl-L-amino acids were synthesized by the method according to the synthetic method for N-succinyl-L-valine mentioned in (2).

Preparation of reaction reagent containing N-succinyl-L-amino acid (1) Preparation of reaction reagent containing N-succinyl-L-tert-leucine 1M HEPES pH 7.9
10 mM $CoCl_2$ solution
150 mM N-succinyl-L-tert-leucine
The above-mentioned 1 M HEPES (2.0 mL), 10 mM $CoCl_2$ solution (0.1 mL) and 150 mM N-succinyl-L-tert-leucine (1.0 mL) were mixed with water (6.4 mL) to give a reaction reagent.

(2) Preparation of reaction reagent containing N-succinyl-L-valine, N-succinyl-L-phenylalanine, N-succinyl-L-tryptophan, N-succinyl-L-asparagine, N-succinyl-L-aspartic acid, N-succinyl-L-serine, N-succinyl-L-glutamic acid, N-succinyl-L-cyclohexylglycine or N-succinyl-L-4-bromophenylalanine.

The reaction reagent containing the N-succinyl-L-amino acid as such was prepared by the same method as in the preparation of a reaction reagent containing N-succinyl-L-tert-leucine mentioned in (1).

Synthesis of N-succinyl-DL-tert-leucine

Equimolar mixture of D-tert-leucine (manufactured by Tokyo Kasei Kogyo) and L-tert-leucine (manufactured by Tokyo Kasei Kogyo) (10 g) was dissolved in 50 mL of water and 15 g of 20% sodium hydroxide solution (manufactured by Nakarai Tesk), then 8 g of succinic acid anhydride and 15 g of 20% sodium hydroxide solution (manufactured by Nakarai Tesk) were added thereto and the mixture was made to react at 20 to 40° C. with stirring. After the reaction solution was neutralized with hydrochloric acid, it was extracted with ethyl acetate and then concentrated. The concentrate was crystallized by addition of hexane thereto followed by drying to give 14 g of N-succinyl-DL-tert-leucine as white powder.

Preparation of reaction reagent containing N-succinyl-DL-tert-leucine

1M HEPES pH 7.9
10 mM $CoCl_2$ solution
150 mM N-succinyl-DL-tert-leucine
The above-mentioned 1 M HEPES (2.0 mL), 10 mM $CoCl_2$ solution (0.1 mL) and 150 mM N-succinyl-DL-tert-leucine (1.0 mL) were mixed with water (6.4 mL) to give a reaction reagent.

Preparation of N-succinylamino acid racemase (1) Preparation of N-succinylamino acid racemase mentioned in Japanese Patent Application Laid-Open (JP-A) No. 2008-61642

Chromosomal DNA of *Geobacillus stearothermophilus* NCA 1503 strain was purified by the following method. Thus, said strain in one platinum loop was inoculated to an LB liquid medium (a 30 mL test tube being chargeable with 5 mL; 1.0% of polypeptone, 0.5% of yeast extract and 1.0% of NaCl; pH 7.4) and subjected to a shake culture at 50° C. for one night. One mL of the resulting culture product was collected and centrifuged (at 12,000 rpm for 10 minutes at 4° C.) to recover the cells. Chromosomal DNA was extracted from the recovered cells using MagExtractor-genome-kit (manufactured by Toyobo) in accordance with the procedure mentioned in the direction for use. As a result of the above operation, about 20 μg of chromosomal DNA was prepared from the cells obtained from 1 mL of the resulting culture product.

After that, N-succinylamino acid racemase gene (SEQ ID No: 3) derived from *Geobacillus stearothermophilus* NCA 1503 strain was amplified by means of PCR using the prepared chromosomal DNA as a template. As to the PCR primers, there were used a 5' primer shown in SEQ ID No: 4 and a 3' primer shown in SEQ ID No: 5. PCR was then conducted (for 30 cycles where each cycle comprised 94° C. for 15 seconds, 55° C. for 30 seconds and 68° C. for 90 seconds) using those PCR primers and KOD Plus DNA polymerase (manufactured by Toyobo) where the above-prepared chromosomal DNA as a template.

Then an operation was carried out using a cloning kit Target Clone-Plus (manufactured by Toyobo) according to the protocol therefor and the resulting gene was cloned to a vector pBluescript to give a recombinant expression plasmid pBSNAR1. Competent cells of *Escherichia coli* JM 109 strain (manufactured by Toyobo) was transformed using the pBSNAR1 to give a transformant. The resulting transformant was named *Escherichia coli* JM 109 (pBSNAR1).

A TB medium (500 mL) was placed in two 2-liter Sakaguchi's flasks, autoclaved at 121° C. for 20 minutes and allowed to cool and ampicillin and isopropyl-β-D-thiogalactoside which were separately subjected to aseptic filtration were added thereto so as to make their final concentrations 100 μg/mL and 0.1 mM respectively. To this medium was inoculated 5 mL of a culture solution of *Escherichia coli* JM 109 (pBSNAR1) cultured at 30° C. for 16 hours in LB medium containing ampicillin (100 μg/mL) followed by culturing at 37° C. for 24 hours with aeration and stirring. After finishing the culture, the cells were collected by centrifugal separation, suspended in 50 mM phosphate buffer (pH 7.5), crushed using a French press and centrifuged again and the supernatant liquid was obtained as a crude enzyme solution. The resulting crude enzyme solution was subjected to removal of nucleic acid using polyethyleneimine and to fractionation using ammonium sulfate, heated at 50° C. for 1 hour and dialyzed with 50 mM phosphate buffer (pH 7.5). Separation and purification were further conducted by column chromatography of DEAE Sepharose CL-6B (manufactured by GE Health Care Bioscience) and octyl-Sepharose (manufactured by GE Health Care Bioscience) each whereupon a pure enzyme specimen was prepared.

Example 1

Preparation of L-Succinylaminoacylase of the present invention

Chromosomal DNA of *Geobacillus stearothermophilus* NCA 1503 strain was purified by the following method. Thus, said strain in one platinum loop was inoculated to an LB liquid medium (a 30 mL test tube being chargeable with 5 mL; 1.0% of polypeptone, 0.5% of yeast extract and 1.0% of NaCl; pH 7.4) and subjected to a shake culture at 50° C. for one night. One mL of the resulting culture product was collected and centrifuged (at 12,000 rpm for 10 minutes at 4° C.) to recover the cells. Chromosomal DNA was extracted from the recovered cells using MagExtractor-genome-kit (manufactured by Toyobo) in accordance with the procedure mentioned in the direction for use. As a result of the above operation, about 20 µg of chromosomal DNA was prepared from the cells obtained from 1 mL of the resulting culture product.

After that, L-succinylaminoacylase gene (SEQ ID No: 1) derived from *Geobacillus stearothermophilus* NCA 1503 strain was amplified by means of PCR using the prepared chromosomal DNA as a template. As to the PCR primers, there were used a 5' primer shown in SEQ ID No: 6 and a 3' primer shown in SEQ ID No: 7. PCR was then conducted (for 30 cycles where each cycle comprised 94° C. for 15 seconds, 55° C. for 30 seconds and 68° C. for 90 seconds) using those PCR primers and KOD Plus DNA polymerase (manufactured by Toyobo) where the above-prepared chromosomal DNA as a template.

Then an operation was carried out using a cloning kit (Target Clone (Registered Trademark)-Plus, manufactured by Toyobo) according to the protocol therefor and the resulting vector was cloned to a vector pBluescript to give a recombinant expression plasmid pLSA1. Competent cells of *Escherichia coli* JM 109 strain (manufactured by Toyobo) was transformed using the pLSA1 to give a transformant. The resulting transformant was named *Escherichia coli* JM 109 (pLSA1).

A TB medium (500 mL) was placed in two 2-liter Sakaguchi's flasks, autoclaved at 121° C. for 20 minutes and allowed to cool and ampicillin and isopropyl-β-D-thiogalactoside which were separately subjected to aseptic filtration were added thereto so as to make their final concentrations 100 µg/mL and 0.1 mM respectively. To this medium was inoculated 5 mL of a culture solution of *Escherichia coli* JM 109 (pLSA1) cultured at 30° C. for 16 hours in LB medium containing ampicillin (100 µg/mL) followed by culturing at 37° C. for 24 hours with aeration and stirring. After finishing the culture, the cells were collected by centrifugal separation, suspended in 50 mM phosphate buffer (pH 7.5), crushed using a French press and centrifuged again and the supernatant liquid was obtained as a crude enzyme solution. The resulting crude enzyme solution was subjected to removal of nucleic acid using polyethyleneimine and to fractionation using ammonium sulfate, heated at 50° C. for 1 hour and dialyzed with 50 mM phosphate buffer (pH 7.5). Separation and purification were further conducted by column chromatography of DEAE Sepharose CL-6B (manufactured by GE Health Care Bioscience) and octyl-Sepharose (manufactured by GE Health Care Bioscience) each whereupon a pure enzyme specimen was prepared. The resulting specimen was confirmed to be a single substance as a result of SDS-PAGE.

Example 2

Confirmation of the Ability of L-succinylaminoacylase of the present invention for the synthesis of L-tert-leucine The L-succinylaminoacylase (2.3 mg/mL, 0.5 mL) prepared in Example 1 was added to the reaction reagent (9.5 mL) containing the above N-succinyl-L-tert-leucine and, after the above was gently stirred, the reaction was conducted at 57° C. for 6 hours. As a control test, the same reaction was conducted by adding 50 mM K-phosphate buffer (pH 7.5) to the reagent mixture in place of the L-succinylaminoacylase solution. After the enzymatic reaction, a sample of the solution was spotted on TLC, developed by a developing solvent (butanol:acetic acid:water=3:1:1) and the resulting L-amino acid was directly qualified by ninhydrin coloring detection test on the TLC.

The result is shown in FIG. 1. In the drawing, the lane 1 shows the product where the L-succinylaminoacylase prepared in Example 1 was used and the lane 2 shows a specimen of L-tert-leucine (manufactured by Tokyo Kasei Kogyo). As is apparent from FIG. 1, the L-succinylaminoacylase of the present invention was able to produce the L-tert-leucine which was identical with the specimen.

Comparative Example

Confirmation of the ability of commercially available L-aminoacylase for the synthesis of L-tert-leucine (1) Synthesis of N-acetyl-L-amino acid L-tert-Leucine (manufactured by Tokyo Kasei Kogyo) (4.7 g) was suspended in glacial acetic acid (manufactured by Nakarai Tesk, 40 mL) and heated at 40 to 50° C. together with addition of thrice molar acetic acid anhydride (manufactured by Nakarai Tesk) thereto whereupon the reaction was conducted. After glacial acetic acid was removed in vacuo, the crude crystals were obtained. After that, the crude crystals were recrystallized from 20% isopropyl alcohol. The precipitate was ground in a mortar and dried to give powder of N-acetyl-L-tert-leucine. Details thereof are mentioned in J. P. Greenstein, *Chemistry of Amino Acids*, 1961, 3.

(2) Preparation of L-aminoacylase

Acylase AMANO (Sigma, code No. 01818-5G) and porcine kidney Acylase I (Sigma, code No. A3010-100MG) were dissolved in 50 mM K-phosphate buffer (pH 7.5) so as to make each of them 2,600 U/mL to give an L-aminoacylase solution.

(1) Preparation of reaction reagent containing N-acetyl-L-tert-leucine

1M HEPES pH 7.9
10 mM $CoCl_2$ solution
150 mM N-acetyl-L-tert-leucine
The above-mentioned 1 M HEPES (2.0 mL), 10 mM $CoCl_2$ solution (0.1 mL) and 150 mM N-acetyl-L-tert-leucine (1.0 mL) were mixed with water (6.4 mL) to give a reaction reagent.

(4) Measurement

The above commercially available L-aminoacylase (Comparative Example 2) (0.5 mL) was added to the reaction reagent (9.5 mL) containing the above N-acetyl-L-tert-leucine and, after the above was gently stirred, the reaction was conducted at 25° C. for 12 hours. As a control test, the same reaction was conducted by adding 50 mM K-phosphate buffer (pH 7.5) to the reagent mixture in place of the L-aminoacylase solution. After the enzymatic reaction, the L-amino acid was directly detected by TLC and ninhydrin reaction by the same manner as in Example 2.

Result of the TLC is as shown in FIG. 2. In the drawing, the lane 1 is the result where Acylase AMANO (commercially available L-aminoacylase) was used while the lane 2 is the result where porcine kidney Acylase I (commercially available L-aminoacylase) was used. The lane 3 shows the specimen of L-tert-leucine (manufactured by Tokyo Kasei Kogyo). As will be apparent from FIG. 2, the conventional commercially available L-aminoacylase is unable to synthesize L-tert-leucine.

It is apparent from FIG. 1 and FIG. 2 that the L-succinylaminoacylase of the present invention is able to synthesize L-tert-leucine which is a non-natural L-amino acid which has been unable to be synthesized by the conventional L-aminoacylase at all.

Example 3

Synthesis of each of amino acids corresponding to N-succinyl-L-valine, N-succinyl-L-phenylalanine, N-succinyl-L-tryptophan, N-succinyl-L-asparagine, N-succinyl-L-aspartic acid, N-succinyl-L-serine, N-succinyl-L-glutamic acid, N-succinyl-L-tert-leucine, N-succinyl-L-cyclohexylglycine and N-succinyl-L-4-bromophenylalanine using the L-succinylaminoacylase of the present invention N-Succinyl-L-valine, N-succinyl-L-phenylalanine, N-succinyl-L-tryptophan, N-succinyl-L-asparagine, N-succinyl-L-aspartic acid, N-succinyl-L-serine, N-succinyl-L-glutamic acid, N-succinyl-L-tert-leucine, N-succinyl-L-cyclohexylglycine or N-succinyl-L-4-bromophenylalanine is used as an N-succinyl-L-amino acid and a reaction reagent was prepared according to the method for the case of N-succinyl-L-tert-leucine. L-succinylaminoacylase of Example 1 was made to react using the resulting reaction reagent to synthesize an L-amino acid and the L-amino acid was directly detected by the same manner as in Example 2.

The result is shown in FIG. 3 and FIG. 4. In FIG. 3, the lane 1 shows the result of detection of the produced L-valine, the lane 2 shows the result of detection of the produced L-phenylalanine, the lane 3 shows the result of detection of the produced L-tryptophan, the lane 4 shows the result of detection of the produced L-asparagine, the lane 5 shows the result of detection of the produced L-aspartic acid, the lane 6 shows the result of detection of the produced L-serine, and the lane 7 shows the result of detection of the produced L-glutamic acid. Also, in FIG. 4, the lane 1 shows the result of detection of the produced L-4-bromophenylalanine, and the lane 2 shows the result of detection of the produced L-cyclohexylglycine.

It is apparent from FIG. 3 and FIG. 4 that the L-succinylaminoacylase of the present invention is able to synthesize the corresponding L-amino acid using any of N-succinyl-L-valine, N-succinyl-L-phenylalanine, N-succinyl-L-tryptophan, N-succinyl-L-asparagine, N-succinyl-L-aspartic acid, N-succinyl-L-serine, N-succinyl-L-glutamic acid, N-succinyl-L-tert-leucine, N-succinyl-L-cyclohexylglycine and N-succinyl-L-4-bromophenylalanine as a substrate.

Example 4

Synthesis of L-tert-leucine from N-succinyl-L-tert-leucine using the L-succinylaminoacylase of the present invention An L-succinylaminoacylase solution (1 mL; 2.3 mg/mL) was added to a 1 wt % solution of N-succinyl-L-tert-leucine (pH 7 to 8; 10 mL; containing 1 mM of $CoCl_2$) and made to react at 57° C. for 90 hours with stirring to give L-tert-leucine. The sample was collected after 16 hours, 42 hours, 65 hours and 90 hours from the start of the reaction and subjected to an HPLC measurement under the following condition to confirm the peaks of succinyl-form compound and free-form compound whereby the synthesis of L-tert-leucine from N-succinyl-L-tert-leucine was confirmed.

Column: Inertsil ODS-2 (particle size: 5 μm; 4.6 mm inner diameter×250 mm length) manufactured by GL Science
Eluant: aqueous solution of phosphate (pH 2.3)/acetonitrile for HPLC=80:20
Flow rate: 0.8 mL/minute
Column temperature: 40° C.
Detection: 210 nm Result of the HPLC measurement is shown in FIG. 5. It is apparent from FIG. 5 that nearly all of N-succinyl-L-tert-leucine (yield: about 90% or more) was able to be converted to L-tert-leucine using the L-succinylaminoacylase of the present invention.

Example 5

Synthesis of L-tert-leucine from N-succinyl-DL-tert-leucine using the L-succinylaminoacylase of the present invention An L-succinylaminoacylase solution (1 mL; 2.3 mg/mL) was added to a 1 wt % solution of N-succinyl-DL-tert-leucine (pH 7 to 8; 10 mL; containing 1 mM of $CoCl_2$) and made to react at 57° C. for 90 hours with stirring to give L-tert-leucine. The sample was collected after finishing the reaction and subjected to an HPLC measurement under the condition same as the Example 4 to confirm the peaks of succinyl-form compound and free-form compound whereby the synthesis of L-tert-leucine from N-succinyl-DL-tert-leucine was confirmed. As a result, the yield was 45% or more and the value near 50% which is the theoretically highest yield was achieved.

Example 6

Synthesis of L-tert-leucine from N-succinyl-DL-tert-leucine using the L-succinylaminoacylase of the present invention and N-succinylamino acid racemase An L-succinylaminoacylase solution (1 mL; 2.3 mg/mL) prepared in Example 1 and the above N-succinylamino acid racemase (0.1 mL; 10.5 mg/mL) were added to a 1 wt % solution of N-succinyl-DL-tert-leucine (pH 7 to 8; 10 mL; containing 1 mM of $CoCl_2$) and made to react at 57° C. for 90 hours with stirring to synthesize L-tert-leucine. The sample was collected after 24 hours and 90 hours from the start of the reaction and subjected to an HPLC measurement under the condition same as Example 4 to confirm the peaks of succinyl-form compound and free-form compound whereby the synthesis of L-tert-leucine from N-succinyl-DL-tert-leucine was confirmed.

Result of the HPLC measurement is shown in FIG. 6. It is apparent from FIG. 6 that nearly all of N-succinyl-DL-tert-leucine (yield: about 85%) was able to be converted to L-tert-leucine using the L-succinylaminoacylase of the present invention and N-succinylamino acid racemase together.

INDUSTRIAL APPLICABILITY

Since the L-succinylaminoacylase of the present invention is able to efficiently produce various natural amino acids and non-natural amino acids such as L-tert-leucine, it is able to be widely utilized for the production of L-amino acids which are useful as intermediates or materials for pharmaceuticals, agricultural chemicals, foods, etc.

SEQUENCE LISTING FREE TEXT

Sequence ID Nos:4, 5, 6 and 7 are the sequences of the primers used in the Examples.

The invention claimed is:

1. An isolated protein, comprising:
a protein consisting of the amino acid sequence shown in SEQ ID No: 2.

2. A process for producing an L-amino acid, comprising:
specifically hydrolyzing N-succinyl-L-amino acid in a mixture of N-succinyl-DL-amino acid using the protein according to claim 1.

3. The process according to claim 2, further comprising:
racemizing N-succinyl-D-amino acid using N-succinylamino acid racemase to produce N-succinyl-L-amino acid.

4. The process according to claim 3, wherein the step of specifically hydrolyzing N-succinyl-L-amino acid in a mixture of N-succinyl-DL-amino acid, and the step of racemizing N-succinyl-D-amino acid using N-succinylamino acid racemase to produce N-succinyl-L-amino acid are conducted simultaneously.

5. The process according to claim 2 wherein N-succinyl-DL-amino acid is N-succinyl-DL-tert-leucine.

6. The process according to claim 3, wherein N-succinyl-DL-amino acid is N-succinyl-DL-tert-leucine.

7. The process according to claim 4, wherein N-succinyl-DL-amino acid is N-succinyl-DL-tert-leucine.

8. A solution, comprising:
the protein of claim 1,
wherein the solution specifically hydrolyzes N-succinyl-L-amino acid in a mixture of N-succinyl-DL-amino acid.

* * * * *